United States Patent [19]

Clayton

[11] Patent Number: 5,074,842
[45] Date of Patent: Dec. 24, 1991

[54] SCHEDULED BOWEL MANAGEMENT SYSTEM

[76] Inventor: Ralph S. Clayton, 305 W. Water St, Ripley, Miss. 38663

[21] Appl. No.: 555,033

[22] Filed: Jul. 20, 1990

[51] Int. Cl.$^5$ ............................................. A61M 3/00
[52] U.S. Cl. ........................................ 604/54; 604/28; 604/262
[58] Field of Search ................... 604/54, 28, 257, 262

[56] References Cited

U.S. PATENT DOCUMENTS

| | | | |
|---|---|---|---|
| 3,495,595 | 2/1970 | Soper | 604/28 |
| 3,924,634 | 12/1975 | Taylor et al. | 604/54 X |
| 4,403,982 | 9/1983 | Clayton | 604/28 |
| 4,406,655 | 9/1983 | Clayton | 604/257 |

*Primary Examiner*—William H. Grieb
*Attorney, Agent, or Firm*—Larson and Taylor

[57] ABSTRACT

A system for scheduling and controlling the maintenance and functioning of the large bowel in fecally incontinent patients is provided which comprises inducement of a multi-day period of constipation followd by administration of colon sweeping procedure which completely empties the contents of the entire colon. The scheduled complete emptying of the colon using the technique of the present invention will greatly reduce the time, effort and cost involved in the care and treatment of fecally incontinent patients, reduce the risk of infection, and maximize the safety, health, comfort and sanitation of the patient and his environment. An apparatus is also provided in the invention which is tailored to be used in the present system, and which will allow for a complete emptying of the entire colon in a safer, more comfortable, and more effective manner than previously possible.

30 Claims, 2 Drawing Sheets

SCHEDULED BOWEL MANAGEMENT SYSTEM

FIELD OF THE INVENTION

This invention relates to a method and apparatus for controlling and scheduling the functions of the human colon in order to prevent or eliminate fecal incontinence.

BACKGROUND OF THE INVENTION

Fecal continence is the ability to defer defecation until an appropriate time at an appropriate place. Fecal incontinence is the inability to defer defecation, commonly present in the elderly, spinal cord or head injury patients and other disabled persons, and in persons having other generalized diseases or abnormalities of the rectum or perineum. For a thorough summary of diagnoses of fecal incontinence by type of disease and area of dysfunction, see Schiller, "Fecal Incontinence" in *Gastrointestinal Disease*, (Fourth Ed., 1989), pg. 323.

There are many degrees of fecal incontinence, from complete lack of control of defecation, even with solid stool, to continuous dribbling of liquid stool in persistent and long standing diarrhea, to even occasional, intermittent slight soiling of clothing associated with acute attacks of diarrhea. At present, management of complete fecal incontinence consists principally of keeping the patient in diapers. The passage of stool is identified by the patient, if mentally competent enough to recognize it, who then informs an attendant. Otherwise, the odor of the stool in the vicinity of the patient or the regular visual check of the diaper are the usual means of learning that stool has been passed by the patient.

This practice, however, is extremely troublesome and unhealthy because even though solid or semi-formed stool can be captured fairly effectively by a diaper, stool frequently is squashed forward and backward between the buttocks and then onto and around the external genitalia and down the legs of the patient. Diarrheal (liquid) stool may leak or flow outside the diaper and onto the bed, and up the back of the patient and down along the legs. An even further problem is presented when a patient is seriously impaired mentally, in that he or she may reach down inside the diaper, grasp the stool, and smear it onto the rest of the body, including regions such as face and hair, or onto the bed before such practice is discovered.

It is clear that problems associated with the diaper system of managing fecally incontinent patients are substantial in a number of ways. For instance, the clean-up alone associated with such incidents requires a complete bath for the patient, a complete change of bed linens and clothing, and a complete cleaning of the bed frame which may be contaminated with stool not readily visible. Further, the inevitable spread of fecal contamination by a diaper may cause infection of the skin of the perineum, external genitalia, buttocks, legs, arms, head and lower trunk of the patient, and may contribute to the creation and persistence of decubitus ulcers or bed or pressure sores. Extensive bathing and re-bathing of the patient, changes of bed linen and the patient's clothing, and procedures necessary to combat the spread of infection are all extremely expensive both in terms of health care worker's time and hospital supplies.

The problem of incontinence is one that has far reaching effects on society in general as well. Fecal incontinence is often the major factor in the decision to institutionalize an elderly or otherwise impaired family member. Often, these patients require two to three times the amount of nursing care that similar but continent patients need. It is estimated that the care of institutionalized incontinent patients in the United States alone costs approximately eight billion dollars per year. In England, the prevalence of fecal incontinence in the general population has been estimated to be as high as 0.4 percent in general, and between 1.0 and 1.3 percent in the elderly population (i.e., those over 65 years old). In other studies, as many as fifty percent of institutionalized patients were observed to have fecal incontinence. Clearly, the problem of institutionalizing incontinent family members will be alleviated if a method were found that could allow the incontinent patient to be treated simply and effectively at home.

The one major method most commonly used at present in dealing with this problem, the diapering of patients, is not really treatment, but is an attempt to minimize the problem by capturing the stool when it is expelled from the rectum. As indicated above, this method is totally unsatisfactory. However, other methods used presently to treat incontinence have not been satisfactory either.

One non-specific strategy that has been used comprises keeping the colon and the rectum empty of feces by stimulating defecation at regular intervals by use of enemas and/or digital stimulation of the anus and rectum. Unfortunately, present nursing and medical practice texts list only small volume enemas, commonly administered in the left lateral decubitus position. As a result, this procedure will clean only the rectum, sigmoid, and a portion of the descending colon, as has been pointed out in my previous patent, U.S. Pat. No. 4,403,982, incorporated herein by reference.

The stimulation of defecation at regular intervals using conventional enema procedures does not cleanse the entire colon at all. After a routine less-than-a-liter enema administered with the patient lying in the left side-down decubitus position, residual stool is often still present in the cecum, ascending colon, transverse colon and descending colon even after defecation following this type of enema. This prior art method thus does not completely empty the entire colon of feces, gas and liquids. As a result, residual matter can remain in the cecum, or ascending or transverse segments of the colon, which then moves distally and can be expelled at any place and time by the incontinent patient.

Still another alternative treatment currently in use is the administration of anti-diarrheal drugs and a low residue bland diet which are used to arrest diarrhea. Although these methods are useful in reducing the expulsion of liquid stool from the colon, they present a serious risk of causing the development of fecal impactions in the colon, which if located too high can only be reached with a flexible colonoscope. Flexible colonoscopy requires sedation or anesthesia, and these procedures carry their own further risks. Additionally, diagnosis of high impactions, located proximal to the rectum, is often difficult, and may result in dangerous impactions not being diagnosed promptly. Thus, anti-diarrheal drug treatment alone, at present, is unsatisfactory as a method of controlling the problem of fecal incontinence.

It is clear that the conventional methods most commonly used at present have failed to provide a safe, effective, inexpensive and sanitary method for dealing with the widespread problem of fecal incontinence which affects patients having a variety of conditions. It is thus highly desirable to develop a system for managing fecally incontinent patients which can be effective in reducing the many medical and economic problems associated with this condition. Additionally, it is desirable to have a system which will have low risk of harmful side effects, which will afford significant therapeutic benefits to the patient and to society, and which will allow for safer, more effective, and less expensive management of the functions of the colon in a great number of afflicted patients.

SUMMARY OF THE INVENTION

According to the present invention, a system for managing fecally incontinent patients in a safe, effective, and inexpensive manner is provided which comprises the scheduling of the function of the bowel through inducement of constipation for a multi-day period, followed by scheduled administration of a colon sweeping procedure employing an apparatus provided by the present invention in a manner so as to completely empty the entire colon of feces, gas and liquids, and virtually eliminate fecal incontinence episodes between scheduled colon sweepings. The complete emptying of the colon will preferably occur at scheduled intervals such as every three or four days. The scheduling technique of the invention will greatly reduce the amount of time and effort that health care personnel will need to spend on incontinent patients, will lower the risk of infection to the patient treated, and will improve the overall sanitation of the health care environment.

In another aspect of the present invention, an apparatus is provided that comprises an improved device for administering a colon sweeping procedure which causes complete emptying of the entire colon, and which has particularly been designed for maximizing safety, effectiveness and comfort to the patient of the procedure of the invention. The device of the present invention comprises a liquid container having a predetermined quantity of fluid sufficient to substantially fill a patient's entire large intestine and an improved tube for introducing the liquid into the patient. The device of the invention also has a soft or "floppy" tip which will easily bend back upon itself if it encounters a mucosal fold in the rectum or if it enters a diverticulum. This "floppy" tip will thus virtually eliminate the risk that the tube employed might perforate the colon mucosa or a diverticulum.

In still another aspect of the present invention, the device provided is designed with instructions so that the rate of flow of liquid into the patient is positively and strictly limited so as to not exceed more than 100 ml per minute, or about 20 minutes for 2,000 ml of isotonic fluid. This feature further maximizes the benefits of the present invention in that the more slowly fluid is infused to distend the colon, the safer, more comfortable, and more effective the present procedure will be.

A further improvement of the present device is that the tube employed to channel fluid into the patient is an integral double-lumen tube having one channel for the sweeping solution and a second channel for injecting and removing air from a specially-shaped balloon which is used to retain the tube in place. This double-channeled tube is an improvement over prior systems which have used completely separate tubes to channel fluid and to inflate the balloon. The feature found in the present invention insures that twisting, kinking or other occlusion of the rubber tube leading to the balloon will not be possible. Thus, occasional difficulty in filling or deflating the balloon will be virtually eliminated.

The scheduling technique and system as provided in the present invention can thus be used effectively to eliminate problems associated with fecal incontinence, and at the same time provide for scheduled therapeutic cleansing of the entire colon in a manner which affords maximum safety and comfort to the patient. Other features and advantages of the present invention will be further described in or inherently obvious from the detailed description provided below.

DETAILED DESCRIPTION OF THE PREFERRED EMBODIMENTS

Figure 1:
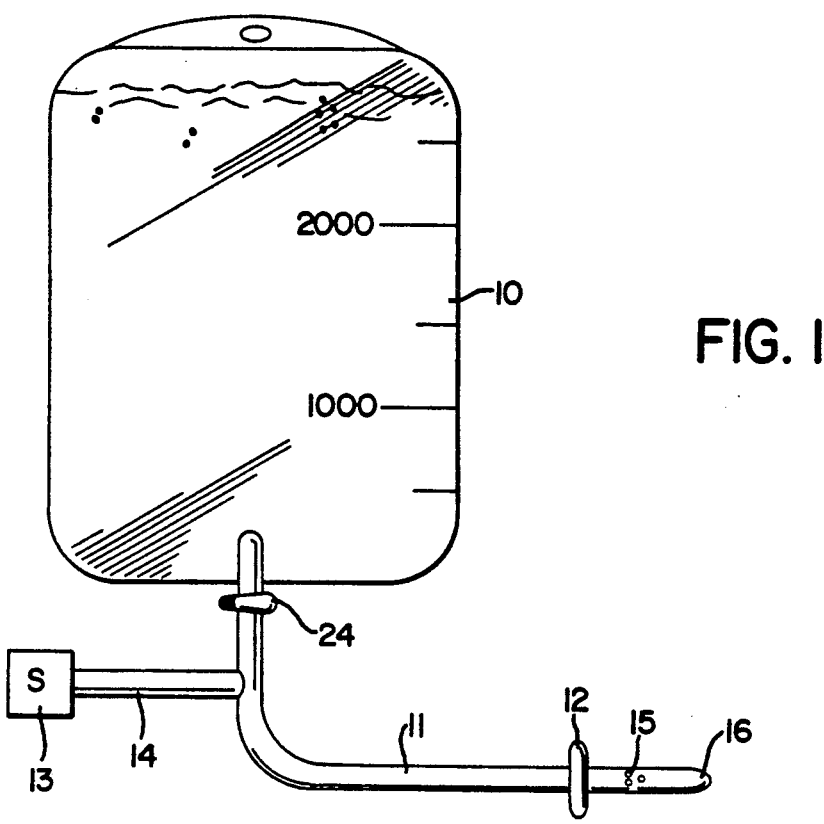
FIG. 1 is a schematic view illustrating certain elements of the present invention.

In accordance with the present invention, a novel system for preventing fecal incontinence in humans is provided which comprises controlling the function of the colon by inducing a state of constipation followed by periodic complete emptying of the entire colon about every two to five days, and preferably about every three to four days, or other suitable period of time as determined by the needs of a particular patient. This system represents the first attempt to control and utilize the ability of the colon to store feces in an effective method for controlling fecal incontinence. The storing of feces in the colon while it awaits scheduled expulsion is a normal bowel function which allows for maximum absorption of salts and water. This storing of feces can be promoted in a number of ways, including administration of anti-diarrheal drugs to the patient, providing the patient with a bland low-residue diet, or modifying the diet to restrict intake of fluids and certain foods. These measures can successfully promote retention of stool, particularly in the ascending and transverse colon.

In prior art methods employing means to promote retention of feces, the major drawback was that only an ordinary (typically less-than-a-liter) enema was given periodically which did not clean the entire colon. As a result, these previous methods allowed for substantial amounts of fecal matter to remain in the cecum, the ascending and transverse segments of the colon, and sometimes even in the sigmoid colon. This constituted a major disadvantage in that these previous methods were not capable of preventing patients from expelling fecal matter from the colon during the period between enemas, without risk of high fecal impaction.

In the present invention, as will be further described below, fecal matter is completely swept from the entire colon during the new cleansing procedure, preferably using the method and apparatus of the invention as will be further described below. As a result, the present technique can be more safely and effectively used to virtually eliminate the problems presently associated with fecal incontinence in a variety of patients. It is contemplated that the scheduling system of the present invention can be conducted on almost any fecally incontinent patient so as to maximize safety and minimize effort and expense presently needed to care for these patients. Further, the system of the invention also maximizes patient comfort and sanitation of the patient's environment while providing therapeutic benefits as well.

In the preferred method of the present system, the entire contents of the colon are swept out using a procedure to be discussed herein, and then a condition of constipation is induced in a fecally incontinent patient for a period of generally about three to four days, depending on the specifics of the patient's condition. This induced constipation is then followed by a complete evacuation of the colon contents using the apparatus and method which will be described herein below. As indicated above, constipation can be induced in a number of ways which will usually depend upon the nature of the patient's disorder as well as his or her age and condition. Preferably, diet modification and the administration of anti-diarrheal drugs such as the anti-cholinergic drugs Lomotil and Loperamide (Imodium A-D) will be used to safely reduce contractions of the colon and effectively induce a condition of constipation in accordance with this invention.

While in the condition of impaired motility or constipation, it is apparent that the patient will not soil himself or the bed sheets, and thus overall hygiene of the patient and the general environment will be vastly improved. After a period of usually about three or four days on a scheduled basis, the patient will be given a special colon cleansing procedure to completely evacuate the large bowel safely and with a minimum of discomfort, as will be discussed further below. Generally, about four hours before sweeping out the contents of the entire colon, the anti-diarrheal drugs will be discontinued. This drug treatment is resumed only after the colon has been swept clean using the method of the present invention.

It is clear that the system contemplated by the present invention will greatly reduce the risks, time, effort and expense involved in patient care in that scheduled colon sweeping is required only once every few days, and accidents between sweepings are virtually eliminated. The scheduling techniques of the system disclosed herein can be tailored to practically any incontinent patient regardless of condition, but will be particularly advantageous in the case of elderly patients, patients with diarrhea and incontinence of various types, and patients with head or spinal cord injuries where normal functioning of the bowel has been impaired. The present invention thus provides a system which not only allows removal of the contents of the entire colon in a safe and effective manner with maximum comfort to the patient, as will be further described below, but one which can be employed in order to comprehensively manage and schedule the functions of the colon to the convenience of patient, staff or attendants. The present system thus greatly reduces the time, effort and cost needed in the care of patients with various colonic disorders, and at the same time provides maximum safety and therapeutic benefits to incontinent patients as well.

In another aspect of the system of the present invention, an apparatus is provided for safely, comfortably and effectively completely removing the contents of the entire colon of the patient. The apparatus of the invention, as observed in FIGS. 1-5, has a number of advantages and improvements which are not disclosed in devices previously used for such a purpose.

The device for carrying out the colon sweeping procedure of the present invention, as observed in FIG. 1, comprises a liquid container 10, preferably a plastic container, e.g., a plastic bag that has been prepackaged with a desired quantity of liquid, preferably distilled water of a controlled mineral content. Additionally, the container can include additives in appropriate concentrations such as polyethylene glycol 3350 (or PEG 3350), a laxative (preferably Bisacodyl), a lubricating and wetting agent (such as castile soap or other suitable wetting agent), suitable electrolytes, and salts and colloids to control osmolality or isotonicity.

Preferably, the fluid used in the present invention will be one which is isotonic and isosmolar with colon mucosa and blood so as to prevent any significant alteration of the total water or electrolytes circulating in the patient's blood. Additionally, this fluid prevents any significant alteration of the concentration of electrolytes in the intercellular or intracellular spaces. An example of a suitable fluid which with added electrolytes can be combined with distilled water to give an appropriate isotonic fluid for use in the present system is polyethylene glycol 3350, which has been used in the oral lavage method of intestinal cleansing. Products employing polyethylene glycol 3350 include Colyte (Reed & Carnrick, Piscataway, N.J.) and GoLytely (Braintree Laboratories, Inc., Braintree, Mass), wherein the PEG 3350 is combined with suitable amounts of sodium chloride, potassium chloride, sodium bicarbonate, sodium sulfate and water before use Colyte and GolLytely do not contain laxatives, but act by fluid volume alone. In the present invention, these isotonic lavage solutions are combined with laxatives and are administered anally, unlike previous methods wherein the polyethylene glycol and other fluids have been administered orally as an intestinal lavage to clear the colon without the addition of a laxative.

It is possible to prepackage the above solid electrolytes in dry form for use in the present invention as an alternative to prepackaging the desired quantity of isotonic liquid. In this embodiment, the pre-packaged dry ingredients are preferably sealed in a plastic container or other package which includes printed instructions so that the colon sweeping fluid can be reconstituted at point of use with the desired volume of distilled water.

As can be further observed in FIG. 1, extending down from the container 10 is the flow tube 11 onto which is attached a specially-shaped balloon 12 designed to retain the tube in the rectum and which can be inflated after the tube is inserted. Air to the balloon is delivered through a syringe valve 13 into line 14, which communicates with an air passage 20, as best observed in FIGS. 2 and 3. This configuration provides an integral double-lumen tube having one lumen or channel which allows the colon sweeping solution to enter the patient, and a second channel which delivers or removes air from the balloon 12 used to retain the tube in place. As a result of this double-channel tube, the present invention constitutes an improvement over prior art systems which use separate tubes to the balloon and to the lumen of the colon in that twisting and kinking or other occlusion of the rubber tube leading to the balloon will be virtually eliminated. The present system thus greatly reduces the possibility that the tube to the balloon will obstruct, hindering injection or removal of air from the balloon.

The air passage 20 is integral with the tube 11 and receives air from line 14 which is delivered into the balloon 12. The balloon itself is preferably made of a plastic, flexible and distensible but non-stretchable material so that its fully expanded shape and size are positively controlled and determined. When air is removed from the balloon 12, it simply collapses and lies along the side wall of tube 11, as best observed in FIG. 4. As indicated above, the dual-channeled nature of tube 11 insures that obstruction to inflation or deflation of the balloon will not occur.

Figure 2:
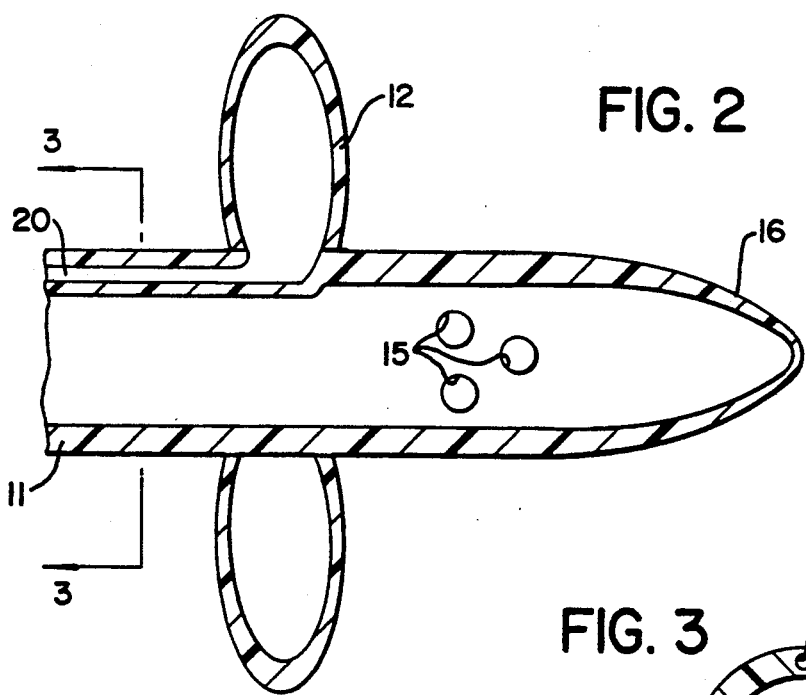
FIG. 2 is an enlarged axial cross-sectional view of the end of the tube shown in FIG. 1.
Figure 3:
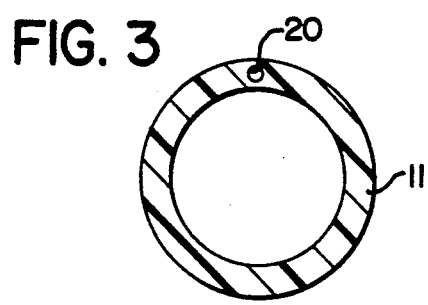
FIG. 3 is a cross-sectional view taken along line 3—3 of FIG. 2.
Figure 4:
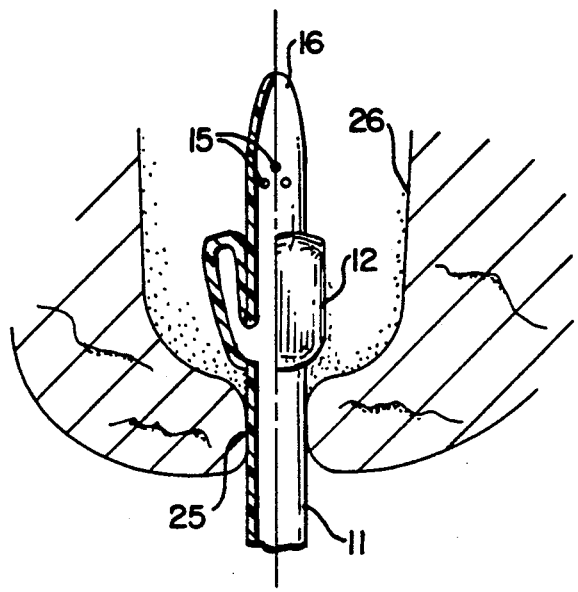
FIG. 4 is a schematic view of the anal opening and the rectum of a patient including the tube of the present invention inserted therein, with a left-hand portion shown in section.

With particular reference to FIGS. 2 and 4, the tube 11 of the present invention is relatively flexible and thin walled in construction, and has a "floppy" distal segment or tip 16. It is preferred that the floppy segment of the tube be straight upon entering the colon unless subject to resistance, such as upon entering a diverticulum or encountering a fold of the mucosa or inner lining of the colon. As a result of having this "floppy" tip, the tube of the present invention has virtually eliminated the risk that it might perforate a diverticulum it may enter. Preferably, the tube will have a wall thickness of roughly 0.5–4.0 mm, and it will preferably be comprised of polyethylene, rubber or other similar material. The floppy tip 16 connected to tube 11 will be sufficiently "floppy" that although it will stand up or align on its own, it will also easily bend down along the side of the main tube unless urged outwardly by the force of the liquid in the tube 11. The floppy tip 16 may be integral with the material of the tube 11 and can comprise a portion thereof which is drawn much thinner. Preferably, tip 16 will have a wall thickness of about 0.1–1.0 mm. Alternatively, a separate flexible material may be adhered to the end of the tube, preferably in such a manner that the exterior surfaces merge smoothly together.

The liquid from the container 10, passing through the tube 11, passes out from the tube and into the rectum of the patient through one or more openings 15 in tube 11. The openings 15 are preferably designed such that under the low pressure head of fluid in the container 10, they permit only the desired rate of flow of liquid. This feature further ensures maximum safety and comfort to the patient.

In a typical apparatus to be used in accordance with the present invention, it will be desirable to limit the flow of fluid into the patient to no more than about 100 ml per minute, or a total of about 20 minutes for a 2,000 ml total volume colon cleansing procedure. This is a relatively long time for filling of the large intestine, but this feature will provide much greater safety and comfort to the patient, and will reduce the pain which can be caused by too rapid filling of the large intestine. The limited flow will also reduce the risk of autonomic dysreflexia, which may occur with upper thoracic levels of spinal cord interruption or transection. The benefits of the present system are maximized in that the slow dispensing of fluid into the patient to distend the colon is much safer, more comfortable, and much more effective than previous procedures.

It is also contemplated that printed in very large red block letters on both sides of the fluid reservoir or bag 10 will be warnings posted not to try to increase the rate of flow of fluid into the patient by squeezing the bag or by any other method whatsoever. It is intended that the fluid will flow into the patient under the force of gravity alone, and an approximately 18" vertical height of the fluid reservoir above the rectum is desirable to achieve this flow. The prominent warning on the fluid reservoir should be emphasized at every possible point throughout the instructions for the use of the present system in administering complete colon sweeping of patients and for preventing fecal impaction.

The advantages of the scheduled bowel maintenance techniques described above are maximized by employing the apparatus of the invention and carrying out a complete colon sweeping procedure which will empty the entire colon of its contents. In the preferred method of the invention, the operator, i.e., a nurse, orderly, or other health care professional, will select the correct container 10 as directed by the physician, having a suitable isotonic liquid therein appropriate for the particular patient. It is alternatively possible that the container will contain dry ingredients which are reconstituted into the osmotically balanced isotonic liquid used in the present system by the addition of an appropriate amount of distilled water, typically around 2,000 ml. The volume of fluid needed in a particular patient can be measured and determined by means of a single contrast barium enema. In cases of smaller patients or patients whose colon volume has been reduced by surgery or disease, so that 2,000 ml may be excessive in that particular patient, then the excess volume of fluid is discarded first, preventing the infusion of excessive volume of fluid. Each bag would normally be supplied with a tube 11 which is supplemented by line 14 coming from a spring loaded syringe valve 13 which can be used in inflating balloon 12. Liquid flow into the tube 11 can be prevented by a suitable clamp 24, as observed in FIG. 1.

With reference to FIG. 4, the distal end of the tube 11 would be inserted through the anus 25 of the patient into the rectum 26. Initially, the tube would be inserted far enough to permit the flattened balloon 12 to completely pass above the anal canal and sphincters. At this time, the floppy tip 16 may be folded back and lie against the side of the tube 11, and the balloon 12 would be deflated so as to lie flat against the side of tube 11. Upon initial insertion, it is of course necessary to insert the tube 11 far enough for the balloon 12 to clear the anal opening and anal sphincters. It is therefore possible that during said insertion the distal end of tube 11 will engage the wall of the rectum. It is also possible that the operators of the apparatus push the tube much farther up into the patient than is necessary or desirable. In either event, the distal end of the tube 11 having floppy tip 16 provides a relatively broad soft surface which tends to avoid damaging the wall of the rectum, and/or would move safety around any obstruction it might encounter.

Figure 5:
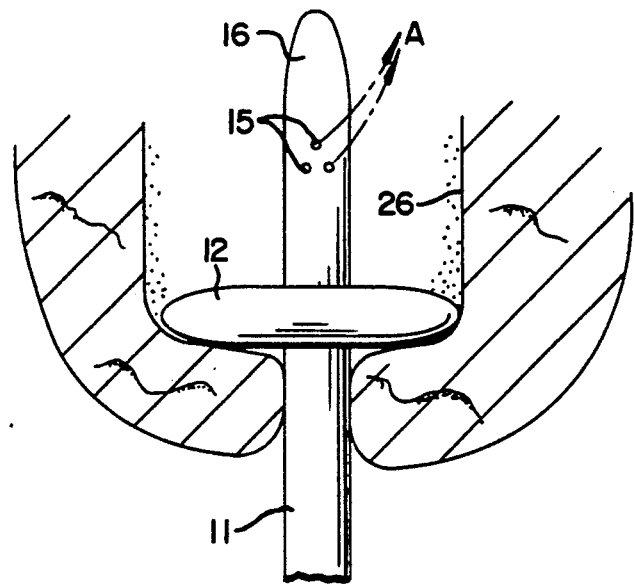
FIG. 5 is a schematic view similar to FIG. 4, but showing the elements of the present invention in a final operative position.

After the tube has been inserted, the balloon 12 is inflated from syringe valve 13 through line 14 and air passage 20 of dual-channel tube 11 to the position as shown in FIG. 5. As illustrated therein, the inflated balloon lies against the floor of the rectum adjacent to the anal opening 25. It takes up very little room in the axial direction, thereby providing a good seal of the anal opening without stimulating the rectum to contract and expel the balloon. After balloon 12 has been inflated and pulled gently down to occlude the lower rectal opening, the liquid is permitted to flow through the tube 11. The pressure head of the liquid from the container 10 allows the liquid to flow through opening 15, as shown by arrow A, and concurrently extends the floppy end 16 as shown in FIG. 5.

At the time that the liquid is being infused, the patient is preferably lying on his left side so that the liquid can easily pass into the rectum, sigmoid and descending colon. The patient is then rolled onto the right side down decubitus position so that gravity causes the fluid to flow downwardly through the transverse colon and then into the ascending colon and cecum. It is also preferable to impart motion during the fluid filling step by any suitable method that will not be harmful to the patient such as gently rolling the patient from side to side, manipulating the abdomen, etc. The technique for manipulating the patient to promote the procedure for filling the entire large intestine from this point has been described previously in U.S. Pat. No. 4,403,982, and reference is made to that description for further details of this procedure. By use of the improved method and apparatus of the present invention, a complete sweep of the colon is thus possible in a safe and effective manner not previously obtainable.

The total system of the present invention as described herein thus provides a system which not only allows complete removal of the contents of the entire large bowel in a safe and effective manner which maximizes safety and comfort to the patient, but which can be employed as well to comprehensively manage and schedule the function of the colon in incontinent patients. The system of the present invention thus represents a significant advantage in reducing the time, effort and expense involved in the care of incontinent patients with various colonic disorders, while providing maximum safety and therapeutic benefits to those patients as well.

Although the invention has been described in considerable detail with respect to the preferred embodiments, it will be apparent that the invention is capable of numerous modifications and variations apparent to those skilled in the art, without departing from the spirit, scope and principles of the present invention.

WHAT IS CLAIMED IS:

1. A method of scheduling the function of the bowel so as to minimize or eliminate fecal incontinence comprising the steps of:
   a) inducing constipation in a patient for a multi-day period;
   b) taking a container of isotonic fluid of sufficient volume to substantially fill the entire large intestine of the patient completely from rectum to cecum, said isotonic fluid containing a laxative and being of a controlled salt and electrolyte composition so as to be isotonic with the patient's body tissues to avoid drawing bodily fluids into the large intestine or permitting fluids to pass from the large intestine into the patient's bloodstream or body tissues;
   c) inserting into the patient's rectum through the anal opening the distal end of a tube which is connected to the container to deliver fluid from the container into the patient, said distal end being sufficiently flexible so that it folds over and presents a broad leading edge so as to avoid damaging of the wall of the large intestine during insertion thereof;
   d) delivering the liquid from the container at a relatively slow rate so as to avoid rapid filling and distension of the walls of the large intestine;
   e) positioning the patient so as to facilitate the isotonic fluid filling the patient's entire large intestine; and
   f) removing the tube and permitting expulsion by the colon of the isotonic fluid and contents of the large intestine which have accumulated during the multi-day period of induced constipation.

2. A method according to claim 1 further comprising the step of completely emptying the colon before initiating the step of inducing constipation.

3. A method according to claim 1 wherein the rate of flow of the isotonic fluid from the container into the patient is not greater than about 100 ml per minute.

4. A method according to claim 1 wherein the container of isotonic fluid having a laxative and controlled salt and electrolyte composition is sealed after the preparation of the isotonic fluid in order to insure that the proper isotonic fluid composition is administered to the patient.

5. A method according to claim 1 wherein the container of isotonic fluid is prepared before the administration to the patient by adding an amount of distilled water to a previously sealed package of dry ingredients comprising a laxative, electrolytes, and polyethylene glycol 3350.

6. A method according to claim 1 further comprising the step of securing the tube in the patient's rectum by inflating a balloon within the rectum positioned against the floor of the rectum just inside of the patient's anal opening.

7. A method according to claim 6 wherein the balloon is relatively thin in the axial direction relative to its outer radial dimension and is of a flexible, non-stretchable material having a maximum inflated volume of less than about 100 ml.

8. A method according the claim 7 wherein the inflated volume of the balloon is about 50 ml.

9. A method according to claim 1 wherein the step of delivering the liquid comprises delivering the liquid through at least one opening near the distal end of the tube.

10. A method according to claim 1 wherein the isotonic fluid contains a lubricating and wetting agent, electrolytes and a laxative.

11. A method according to claim 10 wherein the lubricating and wetting agent is castile soap.

12. A method according to claim 1 wherein constipation is induced for a two to five day period before the patient's large intestine is emptied on schedule.

13. A method according to claim 1 wherein the multi-day constipation is induced by anti-diarrheal drugs and diet modification.

14. A method according to claim 13 wherein anti-diarrheal drugs used to induce constipation are selected from the group of anti-cholinergic drugs consisting of Lomotil and Loperamide.

15. A method according to claim 1 where the volume of fluid needed to substantially completely fill the large intestine of the patient is measured and determined by a single contrast barium enema previous to the initiation of the colon emptying procedure.

16. A method according to claim 1 further comprising the step of imparting motion to the fluid filling of the colon.

17. A method according to claim 16 wherein the motion is imparted by rolling the patient from side to side or manipulating the abdomen.

18. An apparatus suitable for emptying the entire contents of the colon in accordance with the method of claim 1 comprising:

a) a source of fluid of a quantity sufficient to substantially fill the patient's large intestine completely from rectum to cecum;
b) a tube leading from the fluid source to a distal end adapted to be placed in the patient's rectum for delivering the liquid therein, said tube having at least one fluid outlet opening to allow fluid to pass from the inside of the tube into the rectum; and
c) means for retaining the tube's distal end within the patient.

19. An apparatus according to claim 18 wherein the tube includes a distal segment beyond the outlet openings which is comprised of a sufficiently flexible material which easily folds over along the side of the main part of the tube proximal to said distal segment in the absence of pressure within the tube in order to minimize the risk that the tube might perforate the mucosa or a diverticulum that it might encounter in the colon.

20. An apparatus according to claim 19 wherein the main part of said tube has a wall thickness of about 0.5-4.0 mm and the distal segment has a wall thickness of about 0.1-1.0 mm.

21. An apparatus according to claim 19 wherein said means for retaining the tube's distal segment within the patient comprises a balloon attached to the side of the tube which when inflated is relatively thin in the axial direction relative to its transverse diameter.

22. An apparatus according to claim 21 wherein said balloon is comprised of a flexible, non-stretchable material having an inflated volume of less than about 100 ml, and is designed to retain the tube in place in the rectum.

23. An apparatus according to claim 21 wherein the tube has a dual-channel configuration including one air passageway for delivering air into the balloon and a second passageway formed as an integral part of the tube for channeling fluids into the patient's colon.

24. An apparatus according to claim 18 wherein said source of fluid sufficient to substantially fill the patient's large intestine completely from rectum to cecum is sealed in a container.

25. An apparatus according to claim 18 wherein the source of fluid is provided by adding to sealed dry ingredients an amount of distilled water of sufficient volume to substantially fill the patient's large intestine completely from the rectum to the cecum.

26. An apparatus according to claim 25 wherein said sealed dry ingredients comprise a laxative, electrolytes, and polyethylene glycol 3350.

27. An apparatus suitable for completely sweeping out the contents of a patient's entire colon in accordance with the method of claim 1 comprising:
a) a container containing a sufficient volume of fluid to substantially fill the entire large intestine of the patient completely from the rectum to the cecum;
b) a tube leading from the container to a distal end adapted to be inserted into the rectum of the patient to deliver therein the fluid from the container, said distal end of the tube comprising at least one outlet opening which allows fluid to flow outwardly from the tube and into the rectum, and a sufficiently flexible tip located distally beyond the opening, said flexible tip being more flexible than the material of the main part of the tube, and flexible enough to fold over along the side of the adjacent main part of the tube when not supported by liquid under the pressure in the tube;
c) an inflatable balloon made of a flexible, non-stretchable material for holding the distal end of the tube in the patient, said balloon when inflated being relatively thin in the axial direction relative to its outer radius; and
d) an air passageway for delivering air into the balloon and removing air from the balloon, said passageway being formed as an integral part of the wall of the main tube.

28. An apparatus according to claim 27 wherein the fluid in the container comprises a laxative, electrolytes, and polyethylene glycol 3350.

29. An apparatus according to claim 28 wherein the fluid further comprises a lubricating and wetting agent.

30. An apparatus according to claim 29 wherein the lubricating and wetting agent comprises castile soap.

* * * * *